United States Patent [19]
Gie et al.

[11] Patent Number: 5,665,121
[45] Date of Patent: Sep. 9, 1997

[54] PREFORMED MANTLE

[75] Inventors: Graham A. Gie, Lympstone; Peter Lawes, Maidenhead, both of England; Lars Linder, Gävle, Sweden; Robin S. M. Ling, Dittisham, England; Tom J. Slooff, Westerbeek, Netherlands

[73] Assignee: Howmedica International, Shannon, Ireland

[21] Appl. No.: 610,100

[22] Filed: Feb. 29, 1996

Related U.S. Application Data

[62] Division of Ser. No. 377,296, Jan. 24, 1995, abandoned, which is a continuation of Ser. No. 6,882, Jan. 21, 1993, abandoned.

[30] Foreign Application Priority Data

Mar. 3, 1992 [GB] United Kingdom ............ 9202248

[51] Int. Cl.$^6$ ................ A61F 2/28; A61F 5/04
[52] U.S. Cl. ............... 623/16; 606/92; 606/95; 623/18; 623/20; 623/23

[58] Field of Search ............... 623/16, 20, 18, 623/22, 66, 23; 606/95, 94, 93, 92

[56] References Cited

U.S. PATENT DOCUMENTS

| | | | |
|---|---|---|---|
| 4,168,326 | 9/1979 | Broemer et al. | 623/16 |
| 4,846,839 | 7/1989 | Noiles | 623/18 |
| 5,343,877 | 9/1994 | Park | 623/16 |
| 5,385,566 | 1/1995 | Ullmark | 606/95 |

*Primary Examiner*—David Isabella
*Attorney, Agent, or Firm*—Peter C. Richardson; Lawrence C. Akers; Raymond W. Augustin

[57] ABSTRACT

A prosthesis having attachment portion for insertion into or attachment to a patient's bone without bone cement. Parts of the attachment portion on the prosthesis are attached to the bone are covered with a mantle of synthetic resin material and which has a roughened outer surface with bone fragments or calcium phosphate fragments embedded therein.

5 Claims, 8 Drawing Sheets

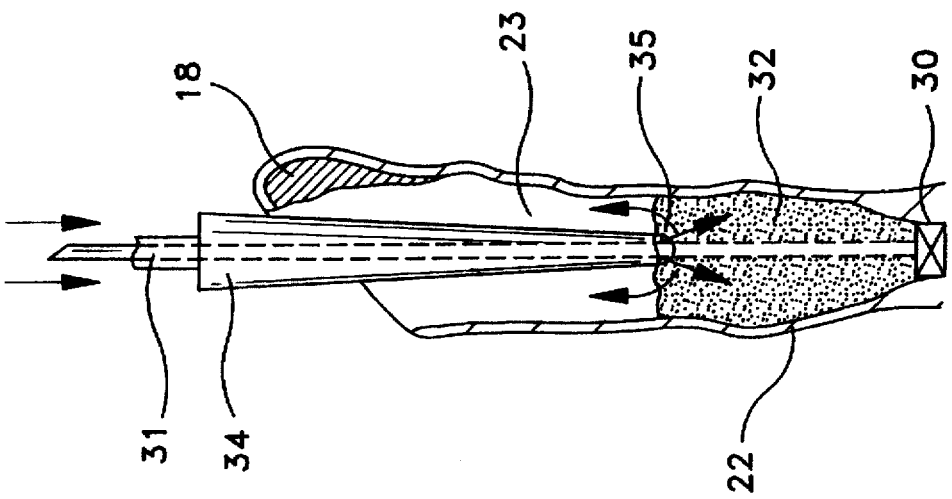
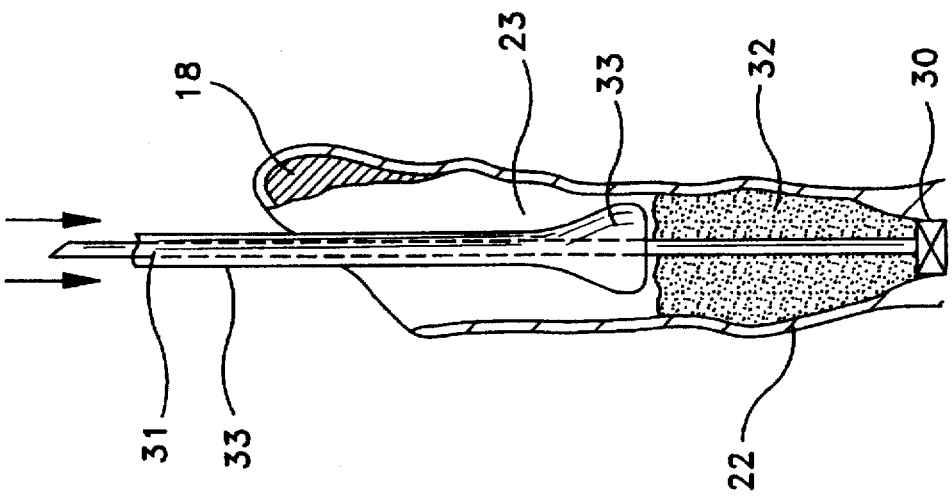
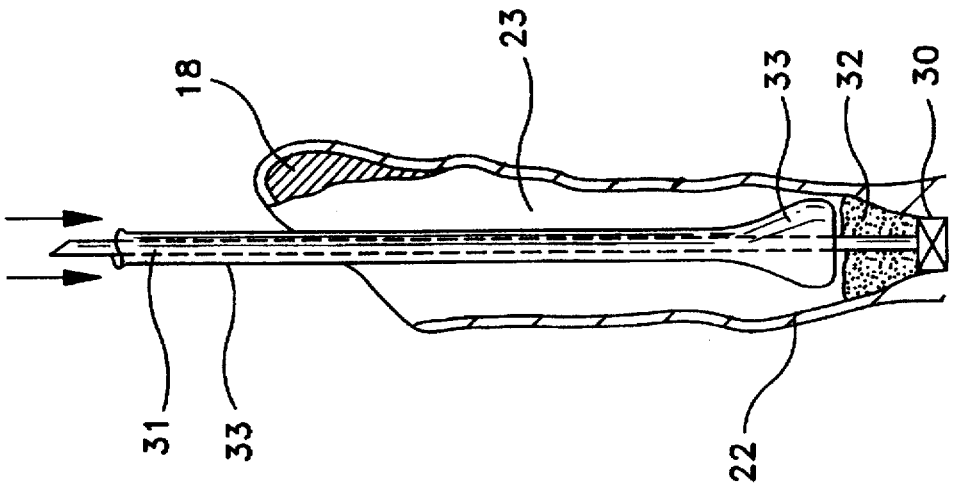

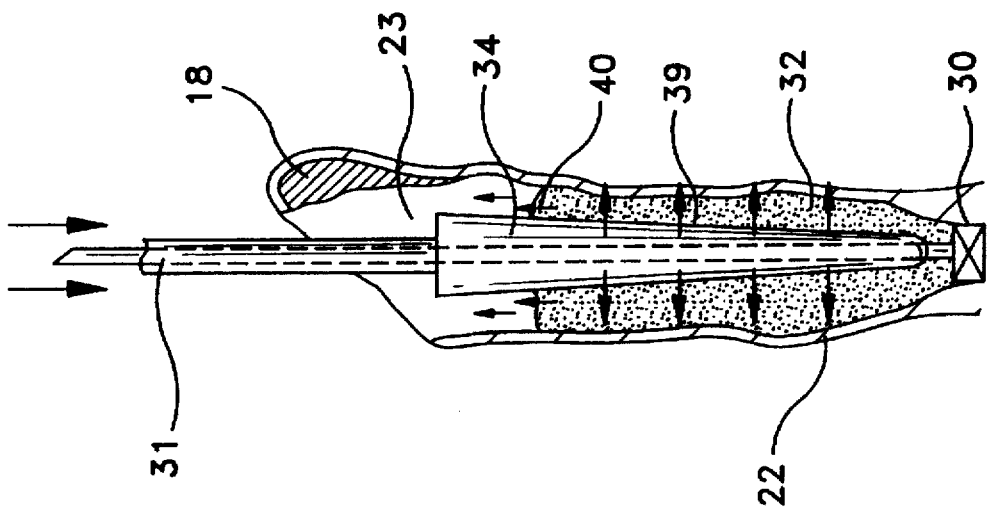
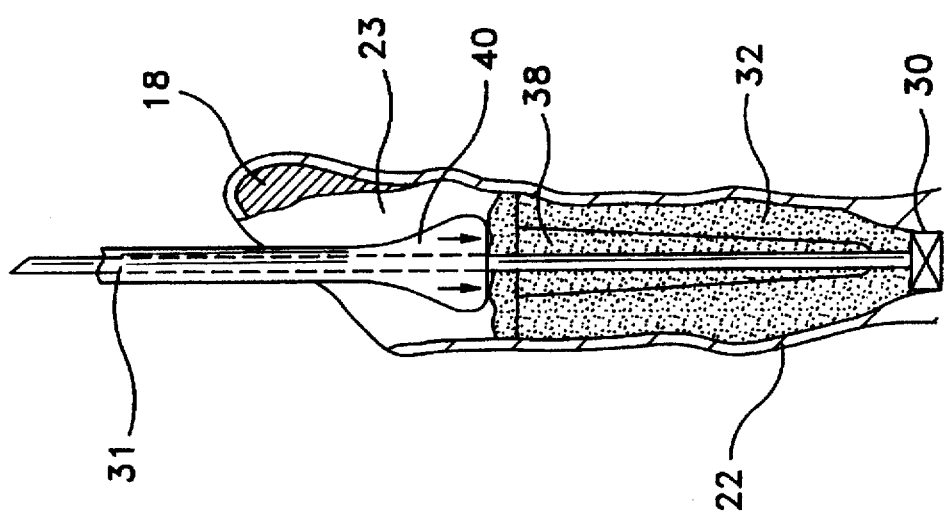
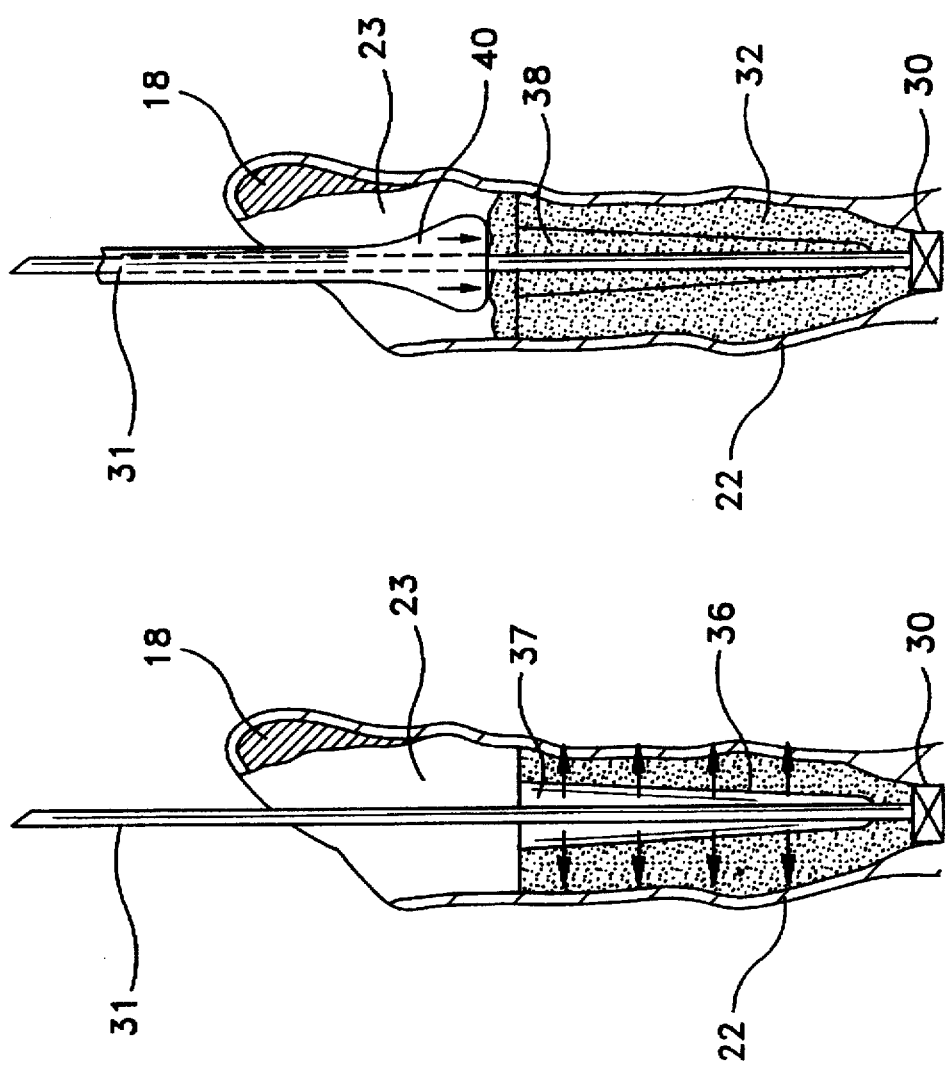

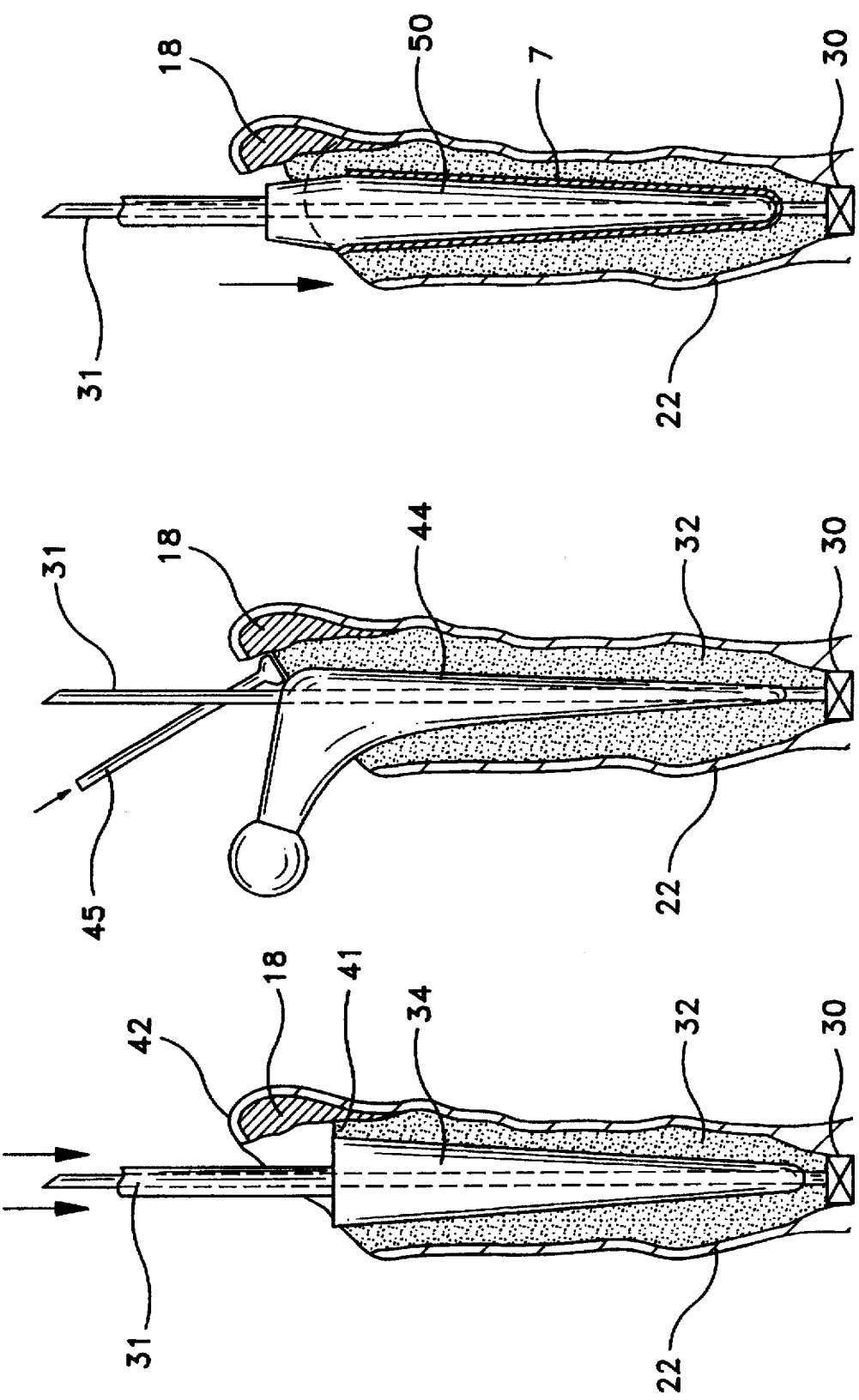

PREFORMED MANTLE

This is a division of application Ser. No. 08/377,296, filed on Jan. 24, 1995 now abandoned, which is a continuation of application Ser. No. 08/006,882, filed on Jan. 21, 1993 now abandoned.

BACKGROUND OF THE INVENTION

1. Field of the Invention

This invention relates to a prosthesis which can be used without bone cement, a preformed mantle for use with such a prosthesis and a method of attaching such a prosthesis to the bone.

2. Description of the Prior Art

U.S. Pat. No. 3,918,100 proposes the use of sputtering to apply a layer of coating material directly onto a metal prosthesis. The process requires complicated and expensive equipment and it is not clear whether it was ever used successfully. The intention appeared to be to coat the prosthesis and then place it in the bone, relying on the coating of bone particles to promote bone growth and attachment to the living bone.

U.S. Pat. No. 4,168,326 relates to a prosthesis covered with an enamel or enamel-like coating to which bioactive material was applied. Once again, the intention was to use the prosthesis without bone cement. This construction also called for expensive and complicated procedures.

U.S. Pat. No. 4,650,489 proposed a prosthesis which was provided with a metallic external sheath. The prosthesis member is attached to the sheath by elastomeric material so that there is a shock absorbing effect. In this construction the sheath is said to have an outer irregular surface to provide for regrowth of bone. It is stated that in the growing process the bone integrates with the sheath resulting in a cancellous or spongy bone. Once again, no cement was used but the whole intention of this device is to provide shock absorbing. The use of roughened surfaces on metallic components in prostheses is of course well known in itself.

U.S. Pat. No. 4,795,472 relates to a hip stem having a polymer coating fixedly attached to a textured surface of the stem.

It is well-known, for example as shown In European Publication No. EP 0 457 464 A1 (U.S. Ser. No. 701,556), the teachings of which are incorporated herein by reference, to provide a prosthesis with a sheath in the form of a preformed cement layer which can be fitted to the implant as a separate component. The purpose of the layer provided by the sheath is to guarantee that there is a minimal cement thickness separating the implant from the bone; and to produce a better implant cement interface for in-service taper re-engagement. In this arrangement the device is assembled to the preformed cement sheath and the surgeon implants the assembly using freshly mixed bone cement.

It is important that there is an effective engagement at the bone cement/bone interface in total joint replacement. If the engagement becomes loose, internal damage occurs to the bone which rapidly accelerates the loosening effect to such an extent that the joint becomes inoperable.

It has been found by experiment that a prosthesis can be implanted with the inside of the opening in the bone filled with bone chips rather than bone cement. A very thin layer of bone cement is provided which separates the implant from the compacted internal bone graft. It has been found that the results are excellent and there is immediate adhesion between the thin layer of bone cement and the adjacent and contacting bone chips.

The present invention is intended to take advantage of the technique referred to above so as to provide a prosthesis and a method of attaching it which eliminates the time consuming and messy operation of handling fresh bone cement during an operation.

SUMMARY OF THE INVENTION

According to one aspect of the present invention a prosthesis is provided with an attachment portion for insertion into or attachment to a patient's bone without bone cement, the parts of said attachment portion which are to be attached to said bone being covered with a mantle of synthetic resin material which has a roughened outer surface. Thus, the invention provides a prosthesis with a mantle to which bone chips can easily engage.

It has been found that when used with internal bone grafting, that is the use of bone chips, it seems as if the bone remodelling process is accelerated. The bone chips are, of course, dead and the body replaces these with living structures remarkably quickly.

A detailed analysis of the bone structure of patients on which bone chips have been used shows how the orientation of the trabecular bone structures have regenerated, not in a normal physiological way, but rather in a direction that responds to the new way in which the load is transferred from the implant to the bone, which of course is different from the original passage or route of load transfer in the original normal joint.

The depth of the roughened outer surface can be between 0.5 to 5 mm and is preferably between 1 and 3 mm. The mantle can be formed and attached to the attachment portion of a prosthesis, but in a preferred arrangement it is preformed before fitting to said attachment portion.

The roughened bone facing surface can be formed by the outer surface of the mantle itself or it can incorporate natural or synthetic bone chippings which may either form the roughened surface themselves or may be located on a previously formed roughened surface. In an alternative construction the roughened outer surface can have a coating of a bioactive material, for example hydroxyapatite or bioglass. Such a bioactive material will tend to combine with the bone chippings used for the internal bone grafting.

The mantle can be made from any suitable material which is biocompatible and thus it can be made from an acrylic material, for example bone cement. As referred to above the mantle can be secured or not secured to the attachment portion of the prosthesis.

Preferably the mantle is dimensioned to enclose said attachment portion from either the distal or proximal extremity of the implant away from the articulating surfaces to a point where it emerges from the bone when in use and is constructed to allow said attachment portion to move further into it under load.

With the above arrangement the end of the mantle away from the articulatory surfaces of the implant can be in the form of a cup, the inner surface of which is spaced away from the adjacent end of the attachment portion, to provide a void when initially located in position to accept subsequent movement between the mantle and the attachment portion after fitting. The invention also incudes a preformed mantle for use with a prosthesis as set forth above.

According to another aspect of the invention a method of attaching a prosthesis of the kind set forth above to a bone includes preparing the surface of the bone to which the prosthesis is to be attached, providing a layer of bone fragments on said surface, and assembling said prosthesis so that the roughened surface of the mantle closely engages said bone fragments.

In a preferred method the mantle is assembled to the prepared layer of bone fragments on the bone surface and the attachment portion of the prosthesis is then assembled to the mantle.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views:

FIGS. 3 to 15 are diagrammatic part cross-sectional representations showing how a hip prosthesis of the kind shown in FIG. 2 can come loose and be replaced by the method according to the present invention;

DESCRIPTION OF THE PREFERRED EMBODIMENT

Figure 1:
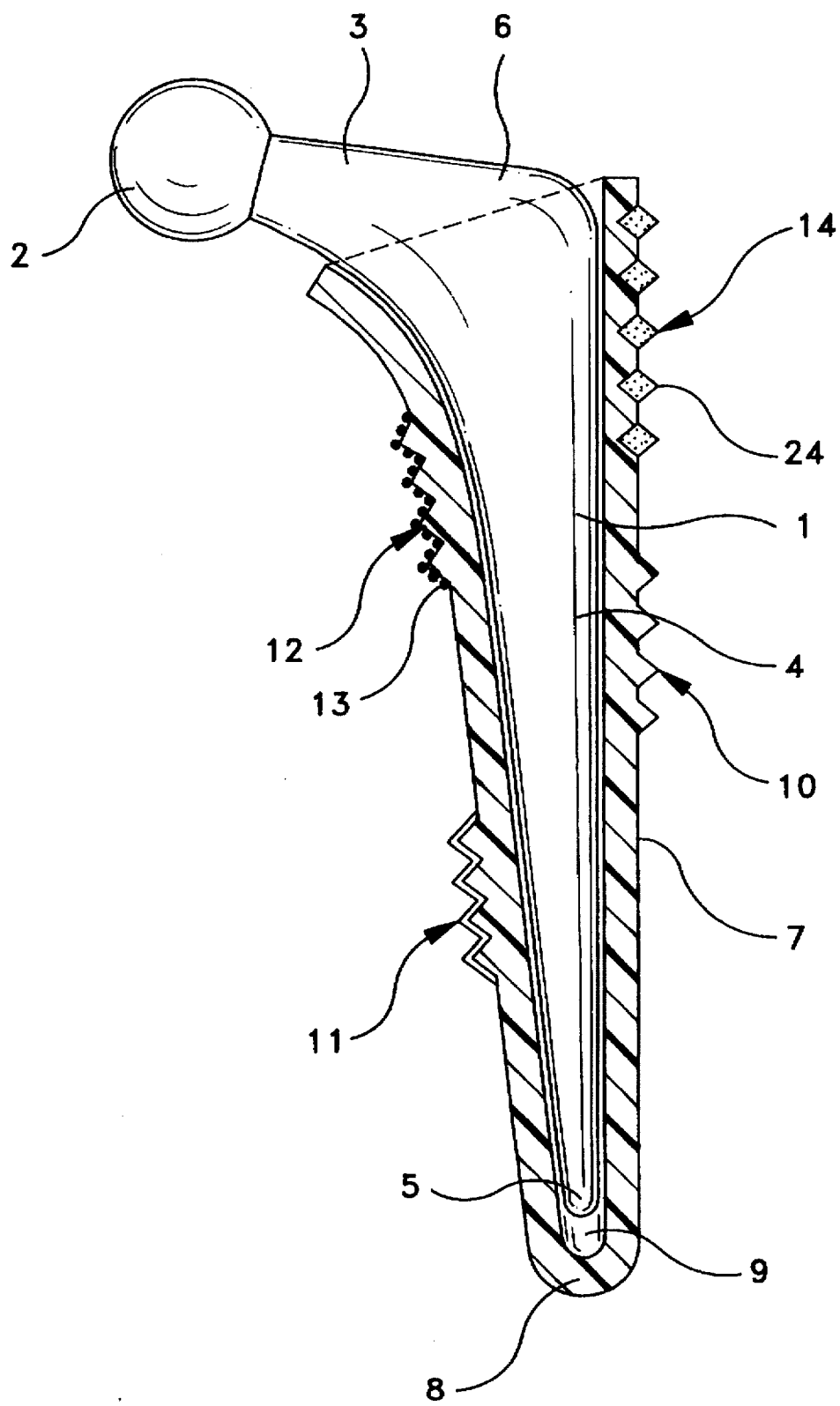
FIG. 1 is a part cross-sectional diagrammatic side elevation of a prosthesis according to the invention and showing different forms of construction for the mantle.

FIG. 1 shows the invention applied in various forms to a prosthetic intramedullary femoral prosthesis which has a head of known type connected through a neck 3 to an intramedullary stem 4. Stem 4 is enclosed from its distal end 5 to a point 6 where it will emerge from the femur in which it is implanted by a mantle 7, which is in the form of an enveloping sheath.

The mantle can be made from any suitable material which is biocompatible and can, for example, be made from an acrylic material such as polymethylmethacrylate which is similar to bone cement material. A filler can be added to make it more flexible. It will be seen that distal end 8 of the mantle is somewhat longer than distal end 5 of stem 4 and is in the form of a cup, the inner surface of which is spaced away from the distal end 5 of the stem 4 to provide a void 9.

The thickness of the mantle can be about 1 mm and although it can be molded on the prosthesis in the embodiments being described it is provided as a preformed item.

The prosthesis is of the shoulderless type and if there is a tendency for it to move further into the mantle this is accommodated by movement within it by movement into the void 9. From the above it will be appreciated that the mantle is not fixed to stem 4, but the stem can move within it.

In a first construction to be described the whole of the outer surface of the mantle is covered with a roughening as indicated by reference numeral 10. The roughening can be patterned or irregular and is between 0.5 and 5 mm deep. The depth of the toughening can vary over the area of the mantle if desired.

In an alternative construction the toughening is provided with a bioactive coating, as indicated by reference numeral 11. Thus a hydroxyapatite coating is provided or the coating could, for example, be bioglass. In an alternative construction particles of hydroxyapatite or tricalcium phosphate or some other calcium phosphate can be embedded into the bone fixation surface provided by the roughening.

Reference numeral 12 indicates another alternative surface in which the surface roughening is covered in bone chips 13. These bone chips can be natural or synthetic bone.

In the above examples of the surface construction the roughness is at least partly provided by a roughening of the surface of the material from which the mantle is made by reference numeral 14 indicates a surface in which the roughness is provided by embedded bone chips or other bioactive fragments 24 which act to provide the roughness themselves. Such bioactive fragments may be materials such as a calcium phosphate like hydroxyapatite.

In the above examples of the surface construction the roughness is at least partially provided by a toughening of the surface of the material from which the mantle is made, but reference numeral 14 indicates a surface in which the roughness is provided by embedded bone fragments 24, which act to provide the roughness themselves.

Any one or a combination of the surfaces described above can be used. The depth of roughness can be between 0.5 and 5 mm but preferably is between 1 and 3 mm although, as mentioned above, it can vary over the area of the mantle.

The method by which a prosthesis with its mantle according to the invention can be used will now be described with reference to FIGS. 2 to 15.

Figure 2:
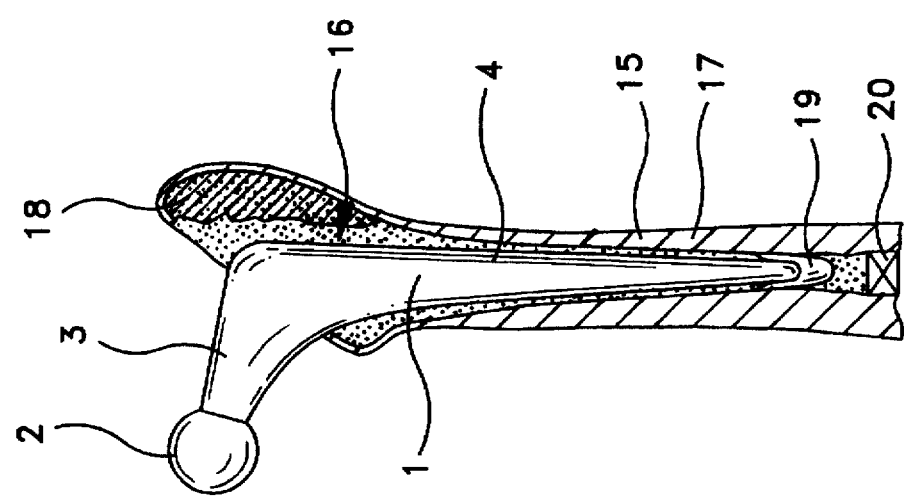
FIG. 2 is a diagrammatic cross-section showing a desired installation of a total hip prosthesis of known kind in a femur.

FIG. 2 shows an idealized primary hip intramedullary femoral prosthesis 1 of the straight tapering collarless polished surface design concept located in a femur 15. The prosthesis has a head 2, neck 3 and stem 4 and is held in place by bone cement indicated by reference numeral 16. The cortical bone 17, of the femur 15, retains some cancellous bone 18. Stem 4 is centralized in the canal by a centralizer 19 of known type and the canal is plugged by a bone plug 20.

Figure 3:
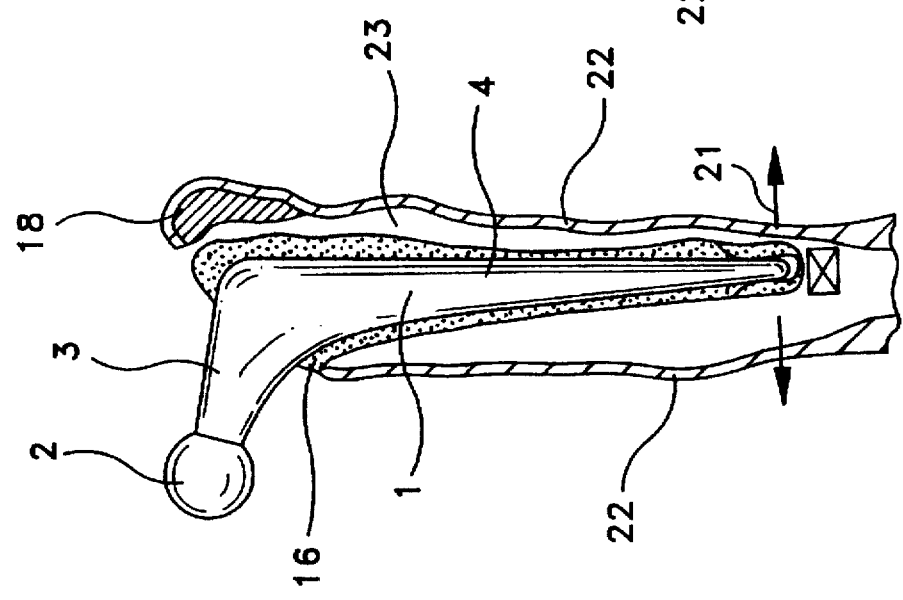

FIG. 3 illustrates what can happen when an implant as shown in FIG. 2 fails. Stem 4 together with the cement 16 break away from the bone and a pendulum effect is produced as shown by arrows 21. This causes severe damage within the bone so that all that is left is a thin cortex 22. A space 23 is created which becomes filled by fluids and fibrous tissues.

Figure 4:
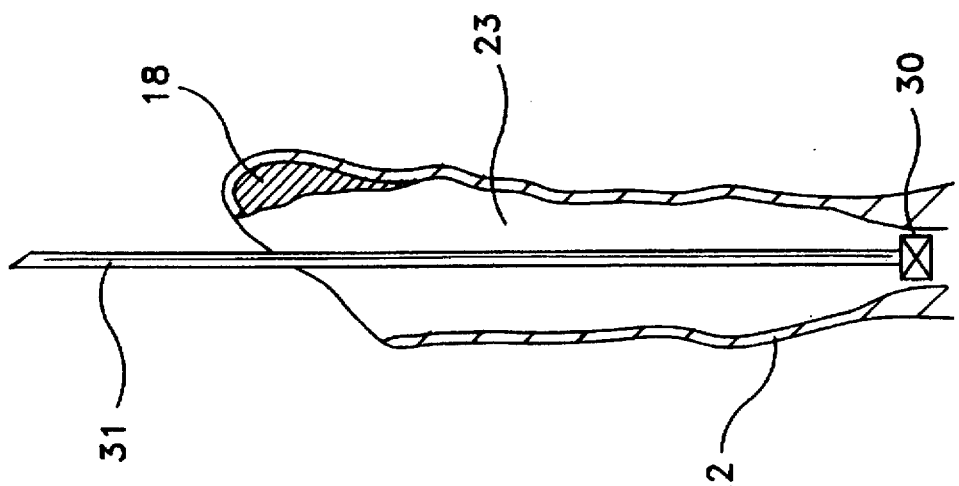

The present invention, however, provides an implant and an implantation method by which the damaged joint can be repaired. The revision procedure commences as shown in FIG. 4 by removing the implant complete with cement and the fibrous tissue by first fitting a bone plug 30 and guide wire 31. Bone chips 32 are now added and compressed using an impactor/ram 33. The bone chips are built up layer by layer to a point about 8 cm below the greater trochanter as shown in FIG. 6. At this point, as shown In FIG. 7, a stem shaped impactor 34 is applied down the guide wire and under impaction dislodges bone chips radially and proximally around the stem, the movement of the bone chips is indicated by reference numeral 35. This movement initiates a cavity for the prosthesis. When the cavity has been formed as shown in FIG. 8, stem impactor 34 is withdrawn. The arrows 36 indicate how bone chips 32 have been radially compressed to leave a cavity 37.

Packing of bone chips now continues as shown in FIG. 9, the additional bone chips being indicated by reference numeral 38. These added chips 38 are now rammed with ram 40 to which hand force is applied to cause compression.

Stem shaped impactor 34 is now reintroduced, as shown In FIG. 10, to again radially compress the bone chips as indicated by arrows 39, the arrows 40 indicating bone chips which are dislodged proximally. Impaction to the stem impactor is applied mechanically.

The actions of filling and compressing are repeated until the bone chip level 41 is 2 cm below the greater trochanter tip 42 as shown in FIG. 11. The space 23 is now filled with bone chips 32. A cannulated trial implant 44 is now inserted into the bone chips, as shown In FIG. 12. as a trial prosthesis and the proximal exposed bone chips are tamped by a tamper 45 to compress them. If desired, extra bone chips can be added proximally. The trial implant 44 is now removed along with the guide wire 31 and a trial prosthesis is inserted. This prosthesis (not shown) is oversized to allow for mantle thickness. The trial prosthesis is removed and the guide wire replaced to guide an introducer 50 carrying a preformed mantle 7 as shown in FIG. 13. The introducer acts to place the preformed mantle 7 in the bone chips, a guide wire 31 acting to accurately centralize it.

Figure 15:
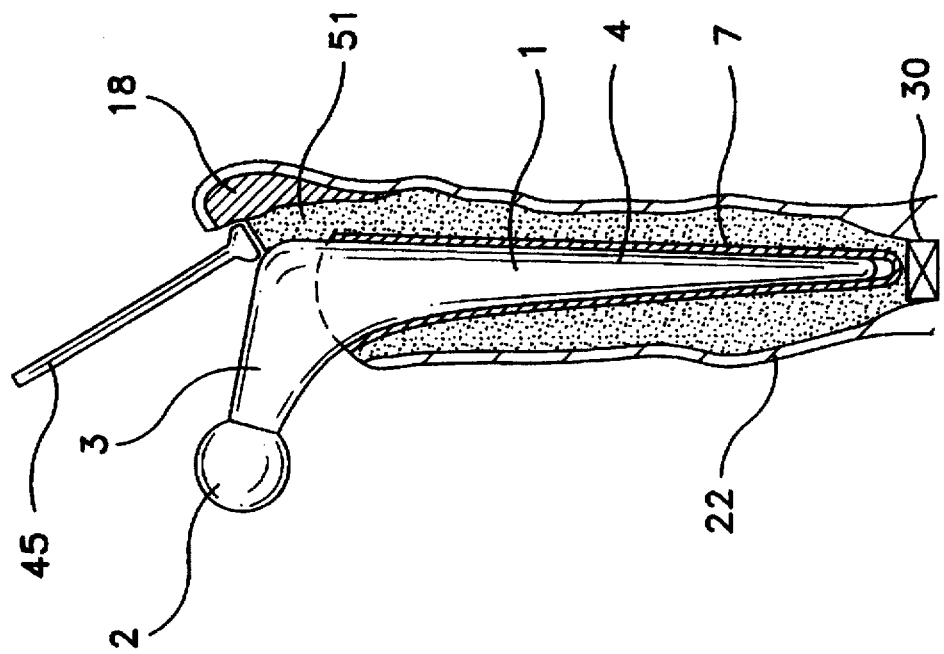
Figure 14:
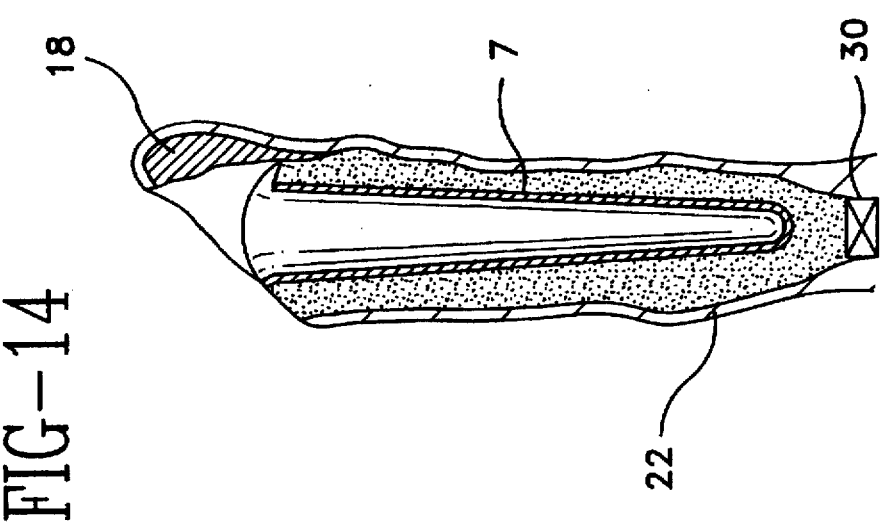

The introducer 50 and guide wire are removed leaving the preformed mantle in situ as shown In FIG. 14. The final stage, shown in FIG. 15, is to implant the femoral prosthesis 1, add further bone chips 41 and tamp them into place with tamper 45.

The bone chips can, for example, be 1 to 2 mm cubed and they can be provided in a variety of shapes and sizes after a pestle and mortar crushing operation. At the small end of the spectrum chips of approximately 1 mm cubed can be found. Long splinters, approximately 0.5 mm by 1 mm by 4 or 5 mm in length can also be produced. It is felt, however, that the chips should not be produced such that a bone slurry is formed. The bone graft, when it is compacted on the inside of the femoral canal, must be mechanically stable and reasonable well consolidated. When the stem with mantle is then pressed into the bone graft, the bone chippings will maneuver slightly as a response to the roughness on the mating surface of the preformed cement mantle. Thus, when the bone chips are later replaced by vital bone, a mechanical lock will result. In the method described above any of the constructions described with regard to FIG. 1 can be used.

Bone chips which are grafted to the bone before the mantle is introduced can either be taken from the patient (autografting) or from another subject, for example obtained from a bone bank, ie. allografting.

Where bone chips are embedded in the surface of the mantle prior to introduction into the patient, this can be allograft bone which is embedded in the cement mantle by the manufacturer. However, it is also possible that the mantle can be made in the operating theater during the course of the bone joint replacement operation by the surgeon or by a theater technician and the patient's own bone (autografting) can be pulverized and embedded in the mantle.

Particles of hydroxyapatite or tricalcium phosphate or some other calcium phosphate can be embedded into the roughened bone fixation surface. Alternatively, the surface roughness can be from a thin bioactive coating layer, for example bioglass, hydroxyapatite or tricalcium phosphate. When no bone chips or particles are embedded in the surface coating layer, these aforementioned materials will assist in giving adequate fixation at the interface. The overall effect of the roughened surface is to provide some degree of immediate fixation to the surrounding bone graft.

From the above it will be appreciated that the operation can be carried out without the use of additional bone cement apart from that which might be used for forming the mantle.

The material from which the mantle is made must be moldable and such that the bone mantle interface is protected and the movement between the implant and the mantle is permitted, in arrangements where this is desirable. It is important that the mantle completely covers the attachment portion of a prosthesis so that any debris generated by movement between the implant and the preformed mantle cannot find its way to the bony interface and become a site for osteolysis (bone death).

In the method described above the implant is to replace an earlier implant which has failed, but it will be appreciated that the method can also be used to implant a prosthesis initially. When the implant is an original one, the space in the bone will of course be of reduced size but the same technique can be used.

Figure 16:
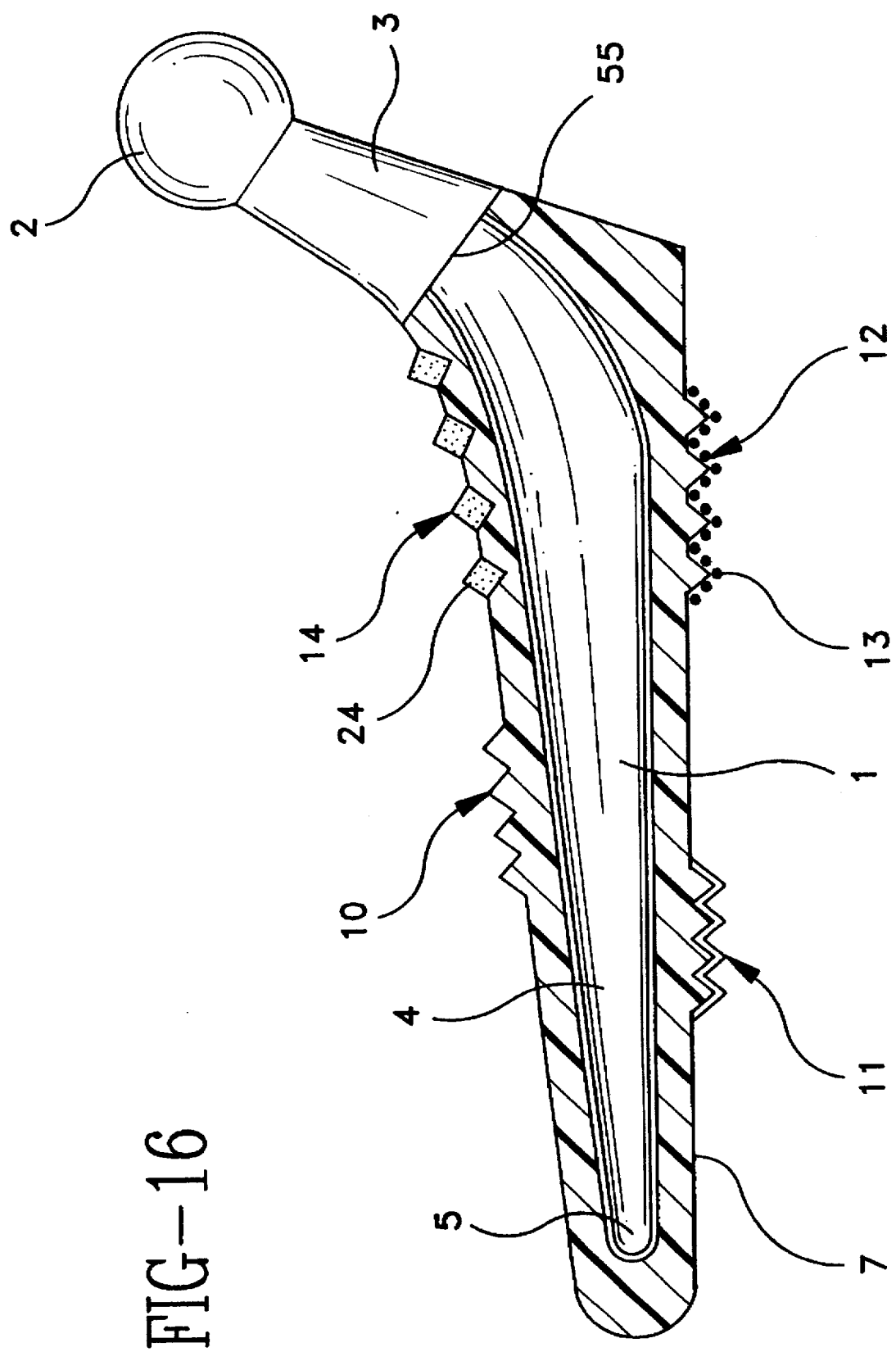
FIG. 16 is a part cross-sectional side elevation of another form of total hip prosthesis embodying the invention in different forms.

FIG. 16 shows a construction similar to FIG. 1 and the same reference numerals are used to indicate similar parts. In this construction, however, the stem 4 is provided with a collar 55 which prevents its sinking into the sheath 7 or the bone when installed.

Figure 17:
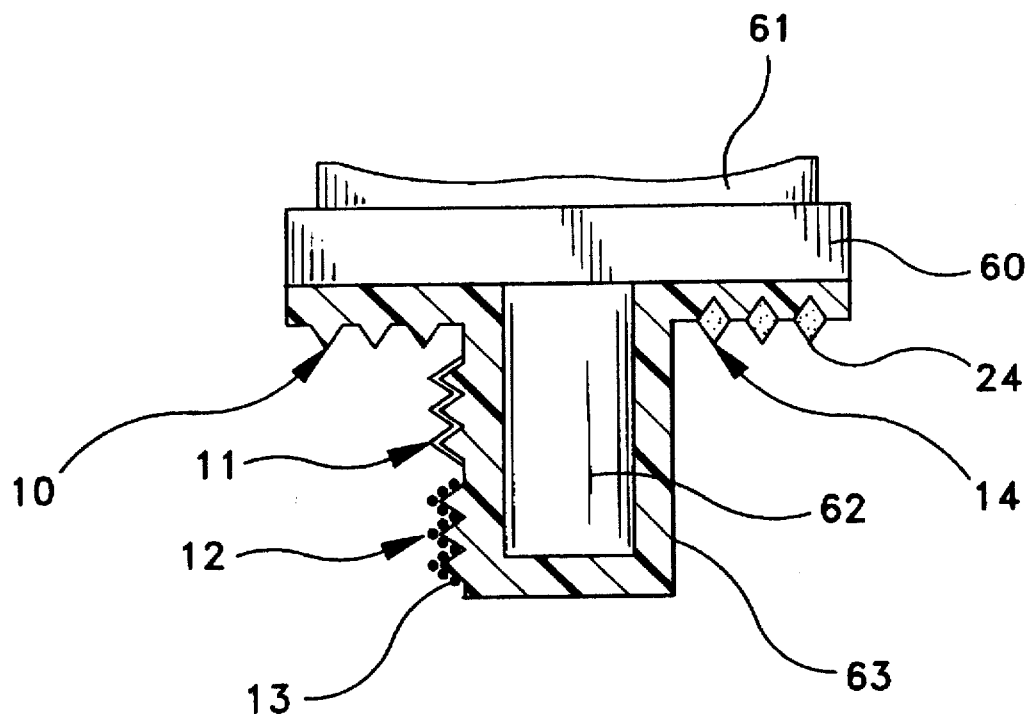
FIG. 17 is a part cross-sectional side elevation of a tibial component of a total knee prosthesis embodying the invention in different forms.

FIG. 17 shows a tibial component of a replacement knee prosthesis which comprises a tray 60, the upper surface of which carries one or more bearing components 61 and the lower portion of which has a stem 62. The lower surface of the tray 60 and the surface of the stem 62 are covered by a mantle 63, which is made from appropriate material and can have any of the surface roughness constructions which are indicated by similar reference numerals to those shown in FIG. 1.

Figure 18:
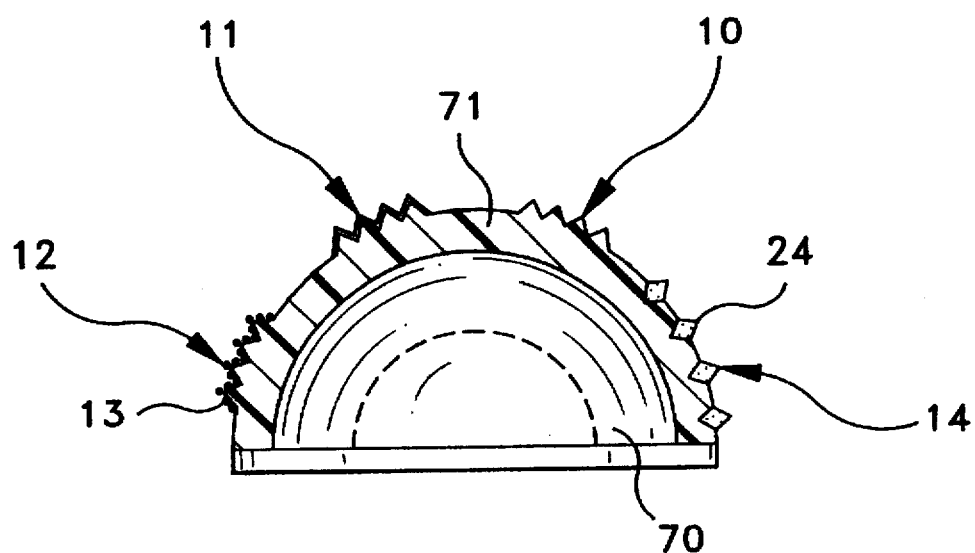
FIG. 18 is a part cross-sectional side elevation of a hip cup embodying the invention in different forms.

FIG. 18 shows an acetabular cup 70, the outer surface of which is again covered with a sheath 71 according to the invention and once again the various ways of providing surface roughness are indicated by reference numerals similar to those used in FIG. 1.

With the construction shown in FIGS. 16, 17 and 18 the same technique for application of the prosthesis to the bone can be used as that described above.

While several examples of the present invention have been described, it is obvious that many changes and modifications may be made thereunto, without departing from the spirit and scope of the invention.

We claim:

1. A method of attaching a prosthesis in a bone canal comprising:

placing the prosthesis within a separate preformed polymethylmethacrylate sheath having a smooth inner and a roughened outer surface, said sheath having an open proximal end and a closed distal end and said inner surface permitting sliding movement of said prosthesis therein, and said sheath having a distal void to permit distal movement of said prosthesis therein;

preparing the surface of the bone to which the prosthesis is to be attached;

providing a layer of bone fragments on said surface of said bone; and thereafter inserting said prosthesis and sheath so that the roughened surface of the sheath closely engages said bone fragments on said surface of said bone.

2. The method as claimed in claim 1 further including the step of placing the sheath into the prepared layer of bone fragments on the bone surface and then placing the attachment portion of the prosthesis into the sheath.

3. The method as set forth in claim 1 wherein said sheath has bioactive fragments embedded therein.

4. The method as set forth in claim 3 wherein said bioactive coating is formed by bone chips.

5. The method as set forth in claim 3 wherein said bioactive coating extends from 0.5 to 5 mm beyond the outer surface of said sheath.

* * * * *